United States Patent

Gosteli et al.

Patent Number: 5,455,363
Date of Patent: Oct. 3, 1995

[54] AMINO ACID DERIVATIVES FOR PEPTIDE SYNTHESIS

[76] Inventors: Jacques Gosteli, Anwilerstrasse 10, CH-4059 Basel; Beat Sax, Auf der Wacht 16, CH-4303 Kaiseraugst; Fritz Dick, Hintergasse 33; Rudolf Tanner, Haupstrasse 74, both of CH-4416 Bubendorf, all of Switzerland

[21] Appl. No.: 957,677

[22] Filed: Oct. 7, 1992

[30] Foreign Application Priority Data

Nov. 10, 1991 [CH] Switzerland ............... 3-001/91

[51] Int. Cl.⁶ .................................................. C07K 7/04
[52] U.S. Cl. .................... 552/104; 530/330; 530/334; 530/336
[58] Field of Search ........................ 530/330, 334, 530/336; 552/104

OTHER PUBLICATIONS

Barlos et al. Tetrahedron Letters vol. 32 No. 4 pp. 475–478 (1991).
Sax et al. Pept. Res. 5(4) 245–246 (1992).
M. Friede et al., Peptide Research, 5 (1992) 145–147.
M: Merler, et al., Tetrahedron Letters, 29 (1988) 4009–4012.
M. Mergler et al., Tetrahedron Letters, 29 (1988) 4005–4008.
D. T. Gist, J. Amer. Chem. Soc., 78 (1956) 5954.
R: Ressler, J. Amer. Chem. Soc., (1956) 5956–5957.
R. Knorr et al., Tetrahedron Letters, 30 (1989) 1927–1930.

*Primary Examiner*—Robert J. Hill, Jr.
*Assistant Examiner*—Carol A. Salata
*Attorney, Agent, or Firm*—Paul & Paul

[57] ABSTRACT

Compounds of formula I are described,

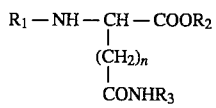

wherein n is equal to one or two, $R_1$ stands for hydrogen or an amino protecting group, $R_2$ represents hydrogen or a carboxyl protecting group and $R_3$ 4-methyltriphenylmethyl, 4,4'-dimethyltriphenylmethyl, 4,4',4"-trimethyltriphenylmethyl. Furthermore described are compounds of formula I which are reactive and suitable for coupling reactions and are derived from I with $R_2$=H by activation of the carboxyl group.

The compounds mentioned above can be used as starting materials for the synthesis of peptides. They are more suitable than analogous compounds of formula I, wherein $R_3$ represents hydrogen or a carbamoyl protecting group used hitherto.

5 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Peptide -continued

```
         ( B ) LOCATION: 1..5
         ( D ) OTHER INFORMATION: /note="Model peptide synthesized
               on Sasrin according to usual solid phase
               technique."

( i x ) FEATURE:
         ( A ) NAME/KEY: Modified-site
         ( B ) LOCATION: 1
         ( D ) OTHER INFORMATION: /label=acetylated ( i x ) FEATURE:
         ( A ) NAME/KEY: Modified-site
         ( B ) LOCATION: 2
         ( D ) OTHER INFORMATION: /label=4- methyltrityl- ( x i ) SEQUENCE DESCRIPTION: SEQ ID NO:1:

Pro  Asn  Gly  Phe  Gly
    1                   5

( 2 ) INFORMATION FOR SEQ ID NO:2:

( i ) SEQUENCE CHARACTERISTICS:
         ( A ) LENGTH: 5 amino acids
         ( B ) TYPE: amino acid
         ( D ) TOPOLOGY: linear ( i i ) MOLECULE TYPE: peptide ( i i i ) HYPOTHETICAL: NO ( i x ) FEATURE:
         ( A ) NAME/KEY: Peptide
         ( B ) LOCATION: 1..5
         ( D ) OTHER INFORMATION: /note="Model peptide synthesized
               on Sasrin according to usual solid phase
               technique"

( i x ) FEATURE:
         ( A ) NAME/KEY: Modified-site
         ( B ) LOCATION: 1
         ( D ) OTHER INFORMATION: /label=acetylated ( i x ) FEATURE:
         ( A ) NAME/KEY: Modified-site
         ( B ) LOCATION: 2
         ( D ) OTHER INFORMATION: /label=tritylated ( x i ) SEQUENCE DESCRIPTION: SEQ ID NO:2:

Pro  Asn  Gly  Phe  Gly
    1                   5
```

AMINO ACID DERIVATIVES FOR PEPTIDE SYNTHESIS

The present invention relates to amino acid derivatives containing N-methyltrityl-carbamoyl groups, their higher homologs and their application in peptide synthesis.

It has been known for long that the carboxylic amide groups of the amino acids asparagine and glutamine often give rise to undesired side reactions in the course of synthesis. (Gish et al. 1956, Ressler 1956, Katsoyannis et al, 1958, etc.).

Protection of the amide function prevents these side reactions. The following groups have found use: 4,4'-dimethoxydiphenylmethyl (Mbs), 2,4,6-trimethoxybenzyl (Tmob) and more recently also the triphenylmethyl(trityl)-protecting group. The latter, in contrast to the others, does not yield side products in the cleavage reaction (Sieber and Riniker, Symposium on Solid Phase Synthesis, Oxford, U.K.; September 1989)

Experience with the trityl (Trt) group indicated the desirability of such a group that could be cleaved faster while still retaining the advantages of the trityl group. It was the task of the present invention to design such a reagent.

The present invention relates to compounds of structure I,

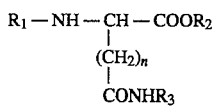

wherein n is equal to 1 or 2, $R_1$ is hydrogen or an amino protecting group, $R_2$ is hydrogen or a carboxyl protecting group, $R_3$ is 4-methyltriphenylmethyl, 4,4'-dimethyltriphenylmethyl, 4,4',4"-trimethyltriphenylmethyl furthermore salts and such derivatives of structure I with $R_2$=H, that are reactive enough to undergo coupling reactions (acylations). The configuration of the chiral carbon atom is arbitrary, it can be either D, L or D,L(racemic).

Compounds of structure I do not, when cleaved, lead to alkylation of tryptophan if this is present in the peptide. They are readily prepared and equally readily cleaved with trifluoroacetic acid or mixtures containing this acid. As regards the rate of cleavage, the compounds of structure I excel the analogous tritylated substances by a factor of two to five. They are, just as the trityl compounds, expecially suited for solid-phase peptide synthesis (SPPS) when used in conjunction with base-labile protecting groups $R_1$ for the protection of α-amino groups, such as the 9-fluorenylmethyloxycarbonyl (Fmoc) group. Of course, any other amino protecting group $R_1$ usually used in peptide synthesis, e.g., acyl residues of carbonic acid half-esters, especially tert.butyloxycarbonyl, benzyloxycarbonyl (optionally substituted), 2-halogenloweralkoxycarbonyl or allyloxycarbonyl are to be considered.

Carbonxyl protecting groups $R_2$ are those usually applied in peptide chemistry, such as lower alkyl, e.g., methyl, ethyl, tert.alkyl, benzyl, nitrobenzyl, methoxybenzyl, benzhydryl, allyl, cycloalkyl, phenyl, βββ-trihalogenethyl, β-triloweralkylsilylethyl, such as β-trimethylsilylethyl.

The group $R_2$ can also function as activating group, in which case such derivatives of formula I can be used for acylation, such as peptide bond formation. Derivatives of this sort are called activated esters; $R_2$ represent an unsaturated residue whose double bond is placed as closely as possible to the carbonyl group, e.g., as in vinyl esters, phenyl esters, substituted phenyl esters, such as pentafluorophenyl esters. Also suitable are other activated esters, such as cyanomethyl esters, thioesters, such as thiophenyl esters, hydroxysuccinimide esters, N-hydroxyphthalimide esters, 1-hydroxybenzotriazole esters.

$R_2$ can be of such nature, that the function —$COOR_2$ in formula I can be regarded as an anhydride. To be taken into consideration are mixed anhydrides, such as the ones obtained by reaction with carbonic acid half-ester chlorides, furthermore symmetrical anhydrides, carboxyanhydrides, anhydrides with inorganic acids, such as acid azides, azolides, iminoanhydrides, as obtained by addition of carbodiimides to a compound of formula I ($R_2$=H). These anhydrides serve the same purpose as activated esters, e.g., acylation.

The abbreviations used for amino acids are the ones in general use. Thus, Asp stands for aspartic acid, Asn for asparagine, Gln for glutamine, Glu for glutamic acids, Ser for serine, Leu for leucine, Gly for glycine, Lys for lysine, His for histidine, Pro for proline, Tyr for tyrosine, Trp for tryptophan, Arg for arginine, Val for valine and Ile for isoleucine.

According to internationally recognized rules of nomenclature the abbreviations for amino acids designate the free acid and, if not indicated otherwise, the one in the L-configuration. The α-amino group is to be imagined on the left hand side of the abbreviation, the carboxyl group on the right hand side. Substituents (protecting groups) in the side-chain of amino acids are appended in brackets to the abbreviation of the respective amino acid. Thus, the term Z-Asn(Mtt)-OH [formerly Z-Asn(MeTrt)-OH] represents the compound of formula Ia.

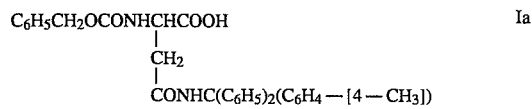

Z=Cbz are usual abbreviations for the carbobenzoxy residue.

Mtt is proposed as abbreviation for the 4-methyltrityl protecting group (4-methyltrityl residue). See also: M. Friede et al., Peptide Research 5, 145 (1992).

The advantages attained by the use of compounds I in peptide syntheses are illustrated in the experimental part. They are based on a more rapid cleavage of the Mtt group compared to the Trt group. See also: M. Friede et al., loc. cit.

Compounds of formula I can be used as building blocks for peptides containing glutamine and/or asparagine or as intermediates for the preparation of these building blocks. For solid-phase peptide synthesis compounds of formula I are used, wherein $R_1$ represents an amino protecting group, such as 9-fluorenylmethyloxcarbonyl (Fmoc) or tert, butoxycarbonyl (Boc), $R_2$ hydrogen and $R_3$ 4-methyltrityl (Mtt) and reactive carboxyl derivatives thereof.

The amide protecting group $R_3$ according to the invention is stable under conditions of catalytic hydrogenation used for the cleavage of the benzyloxcarbonyl group (as $R_1$) or the benzyl group for carboxyl protection (as $R_2$). The protecting group $R_3$ can be cleaved, e.g., with trifluoroacetic acid-dichloromethane (1:1) in the temperature range of −20° to 50° C., such as at +30° C.

Compounds of formula I can be prepared in known fashion. The synthesis procedure is characterized by reaction of a compound of formula II.

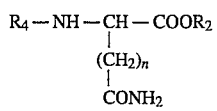   II in which $R_4$ is hydrogen or an amino protecting group stable under the reaction conditions, and both n and $R_2$ express what was mentioned above (under formula I), with a compound of formula III $$R_3OH \quad\quad\quad III$$

whereby $R_3$ as the aforementioned significance. If necessary, protecting groups that do not form part of the desired final product of formula I, are cleaved.

The procedure is detailed in the sequel: The reaction is effected in a suitable organic solvent in the presence both of a catalytic amount of a strong acid, preferably sulfuric acid, and a dehydrating agent, such as acetic anhydride, in the temperature range of 0° and 100° C., preferably between 20° and 70° C., e.g., at 50° C.

The amino protecting group $R_4$ represents a group stable under the acidic conditions, such as trifluoroacetyl or preferably benzyloxycarbonyl or 9-fluorenylmethyloxycarbonyl.

If in the desired final product of formula I $R_1$ and/or $R_2$ represent hydrogen, the protecting groups $R_2$ and $R_4$ have to be cleaved.

Carboxyl protecting groups $R_2$, stable under the reaction conditions, can be removed if so desired, and if $R_2$ represents simple groups such as methyl, ethyl or allyl, by saponification.

Trihalogenacetyl, such as trifluoroacetyl as amino protecting group $R_4$ can be cleaved by mild saponification, such as by sodium carbonate solution. Benzyloxycarbonyl as amino protecting group $R_4$ is cleaved by hydrogenolysis in the presence of a noble metal catalyst, such as palladium on barium sulfate.

9-Fluorenylmethyloxycarbonyl as amino protecting group $R_4$ is cleaved by means of a solution of an amine, such as piperidine in dimethylacetamide.

The overall yields (three steps) amount to about 45% of theory.

Compounds of formula I can be present as salts, especially when $R_1$ and/or $R_2$ is/are equal to hydrogen, or can be converted into salts by addition of acids or bases. Preferentially stoichiometric amounts of these agents are applied to complete the salt formation. Inner salts of formula I ($R_1$=$R_2$=hydrogen) can be prepared from other salts by neutralization of their solutions to the isoelectric point and isolation.

A subject matter of the invention also concerns the use of compounds of formula I, especially the use of those compounds of formula I, wherein $R_1$ represents an amino protecting group, such as benzyloxycarbonyl, tert.butoxycarbonyl or, especially, 9-fluorenylmethyloxycarbonyl, $R_2$ and $R_3$ represent hydrogen and 4-methyltrityl, respectively, as well as the use of reactive carboxylic acid derivatives of these compounds, for the synthesis of peptides, especially on solid phase.

The invention also relates to substances, that contain one or more of the bivalent residue of formula IV,

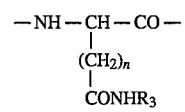   IV in which n equals 1 or 2 and $R_3$ represents 4-methyltrityl. These products are peptide derivatives or peptide fragments, such as the ones that are formed in peptide syntheses as intermediates, they may also be bound to a synthesis resin.

The following examples serve to illustrate the invention, without, however, restricting it in any way.

| Abbreviations used | |
|---|---|
| Asn | asparagine |
| DCM | dichlororpathane |
| Fmoc | 9-fluorenylmethyloxycarbonyl |
| Gln | glutamine |
| Mtt (formerly MeTrt) | 4-methyltrityl |
| OSu | N-hydroxysuccinimide ester |
| TFA | trifluoroacetic acid |
| Z(Cbz) | benzyloxycarbonyl |
| TLC | thin layer |
| HPLC | high performance liquid chromatography |

EXAMPLE 1

Z-Asn(Mtt)OH

The mixture of 66.5 g Z-Asn-OH (250 mM), 137.2 g 4-methyltriphenyl carbinol (500 mM), 750 ml acetic acid and 47 ml (500 mM) acetic anhydride is stirred at room temperature for five minutes. Upon addition of 1.25 ml concentrated sulfuric acid the temperature is raised to 50° C., a clear yellow solution results after 15 minutes. After a total of 2½ hrs the mixture is allowed to cool and poured into 5 l ice-cold water. The formed precipitate is filtered off, washed thoroughly with water and dissolved in ca. 500 ml ethyl acetate. The solution is washed with saturated brine, dried over sodium sulfate and concentrated in vacuo to 300 ml of an oil. Crystallization of Z-Asn(Mtt)OH is induced by addition of diisopropylether.

mp 187°–197° C. Yield 75%.

EXAMPLE 2

H-Asn(Mtt)OH

A suspension of 52.3 g Z-Asn(Mtt)OH (100 mM) in 400 ml methanol and 100 ml 1N hydrochloric acid is hydrogenated at room temperature and normal pressure in the presence of 2 g of a palladium on carbon (10%) catalyst. On completion of hydrogen uptake the catalyst is filtered off, washed with methanol and the filtrate, after addition of 13.9 ml triethylamine (100 mM) and 100 ml water, condensed in vacuo to a volume of about 300 ml. The crystalline precipitate is collected by filtration and washed with water until the washings are chloride-free. The obtained H-Asn(Mtt)OH contains 0.5–1 mole of water and decomposes above 222° C. Yield 80%.

EXAMPLE 3

Fmoc-Asn(Mtt)OH 19.9 g of H-Asn(Mtt)OH.0.5 $H_2O$ (50 mM) are suspended in a solution of 10.6 g sodium carbonate (100 mM) in 125 ml water and 25 ml dioxane. To the stirred suspension is added at room temperature within one hour a solution of 16.9 g Fmoc OSu (50 mM) in 68 ml dioxane. Upon completion of the reaction (overnight), the reaction mixture is diluted with water, extracted several times with ether, the aqueous phase is covered with 400 ml ethyl acetate and acidified with half-concentrated hydrochloric acid (pH 2–3); after equilibration the organic phase is separated, washed with half-saturated brine and dried over sodium sulfate. On concentration in vacuo to an oil (ca. 50 g), crystallization is brought about by addition of ether and diisopropylether. mp 190°–202° C. decomposing. Yield 75%.

EXAMPLE 4

Z-Gln(Mtt)OH

A mixture of 140.14 g Z-Gln-OH (0.5 mole) and 274.4 g 4-methyltriphenylcarbinol (1 mole) in 1.5 l acetic acid and 93.4 ml acetic anhydride (1 mole) is stirred at room temperature for 7 minutes. Upon addition of 2.5 ml concentrated sulfuric acid the temperature is raised to 50° C.; a clear, yellow solution results after 15 minutes. After 2½ hrs the solution is allowed to cool and poured into 5 l ice-cold water. The precipitate formed is filtered off, washed thoroughly with water and dissolved in 1 l ethylacetate. The resulting solution is washed with saturated brine, dried over sodium sulfate and concentrated under reduced pressure to an oil (400 ml) which crystallized on addition of diisopropylether. mp 187°–197° C. Yield 75%.

EXAMPLE 5

H-Gln(Mtt)OH

A suspension of 107.3 g Z-Gln(Mtt)OH (200 mM) in 800 ml methanol and 200 ml 1N hydrochloric acid is hydrogenated at room temperature and normal pressure in the presence of 0.4 g palladium on carbon (10%) catalyst. On completion of the hydrogen uptake the catalyst is filtered off, washed with methanol and the filtrate, after addition of 27.9 ml triethylamine (200 mM) and 200 ml water, concentrated to a volume of about 600 ml. The formed crystalline precipitate is filtered off and washed with water until the washings are chloride-free. The obtained H-Gln(Mtt)OH contains 0.5–1 mole water and decomposes slowly above 231° C. Yield 85%.

EXAMPLE 6

Fmoc-Gln(Mtt)OH 41.15 g H-Gln(Mtt)OH.0.5 $H_2O$ (100 mM) are suspended in a solution of 21.2 g sodium carbonate (200 mM) in 250 ml water and 50 ml dioxane. At room temperature a solution of 33.7 g Fmoc OSu (100 mM) in 135 ml dioxane is added to the stirred suspension within 1 hour. Upon completed reaction (overnight) the reaction mixture is diluted with water, extracted several times with a mixture of diisopropylether-ether (1:1). The separated aqueous phase is covered with a layer of 800 ml ethyl acetate, acidified with half-concentrated hydrochloric acid (pH 2 to 3), equilibrated with the organic phase and the latter washed with half-saturated brine and dried over sodium sulfate. Concentration under reduced pressure gives an oil which is crystallized from ether. Melting above 108° C. (decomposition to 144° C.). Yield 75%.

EXAMPLE 7

Comparative Cleavage Experiments: Trt Versus Mtt

The two model peptides Ac-Pro-Asn(Trt)-Gly-Phe-GlyOH (VI) and Ac-Pro-Asn(Mtt)-Gly-Phe-GlyOH (VII) are synthesized on a 1.2 mM scale on Sasrin according to the usual solid-phase technique. (M. Mergler et al., Tetrahedron Letters 29, 4005 [1988]). 2-[1H-Benzotriazol-(1)-yl]-1,1,3,3-tetramethyluronium tetrafluoroborate is used as coupling reagent (R. Knorr et al., Tetrahedron Letters 30, 1927 [1989]).

In both cases the crude yield (yield of crude peptide) is almost quantitative and the purities are >97% (by TLC and HPLC).

The reactivity of compounds VI and VII are checked against the cleavage reagent TFA/DCM=1:1 (v/v) at 20° C. 5 mg portions of the substances are each treated with 100 µl of the cleavage reagent and the course of the cleavage of the Trt- and Mtt-group, respectively, followed by semiquantitative TLC. A half-life time of 5 minutes is found for substance VI, while a value of approximately 1 minute is observed for substance VII.

We claim:

1. A compound according to formula I:

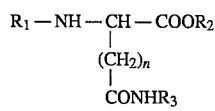

in which n is an integer selected from 1 and 2, $R_1$ is selected from hydrogen and amino protecting groups, $R_2$ is selected from hydrogen and carboxyl protecting groups, and $R_3$ is selected from 4-methyltriphenylmethyl, 4,4'-dimethyltriphenylmethyl, and 4,4',4''-trimethyltriphenylmethyl.

2. A compound according to claim 1 wherein $R_1$ is 9-fluorenylmethyloxycarbonyl.

3. A compound according to claim 1 wherein $R_1$ is carbobenzoxy.

4. A compound according to claim 1 wherein $R_1$ is hydrogen.

5. A salt of a compound according to claim 1.

* * * * *